(12) United States Patent
Hibner et al.

(10) Patent No.: US 11,013,907 B2
(45) Date of Patent: May 25, 2021

(54) SURGICAL DEVICES HAVING CONTROLLED TISSUE CUTTING AND SEALING

(71) Applicant: Ethicon LLC, Guaynabo, PR (US)

(72) Inventors: John A. Hibner, Mason, OH (US); David C. Yates, West Chester, OH (US); Geoffrey S. Strobl, Williamsburg, OH (US); Kevin L. Houser, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 885 days.

(21) Appl. No.: 15/724,696

(22) Filed: Oct. 4, 2017

(65) Prior Publication Data
US 2018/0021562 A1 Jan. 25, 2018

Related U.S. Application Data

(63) Continuation of application No. 14/166,194, filed on Jan. 28, 2014, now Pat. No. 9,802,033.

(51) Int. Cl.
| | |
|---|---|
| *A61B 18/14* | (2006.01) |
| *A61N 1/00* | (2006.01) |
| *A61B 17/32* | (2006.01) |
| *A61B 34/00* | (2016.01) |
| *A61B 17/00* | (2006.01) |

(Continued)

(52) U.S. Cl.
CPC ............... *A61N 1/00* (2013.01); *A61B 17/32* (2013.01); *A61B 18/1442* (2013.01);
(Continued)

(58) Field of Classification Search
CPC ............ A61B 18/1442; A61B 18/1445; A61B 2018/1452; A61B 2018/1455;
(Continued)

(56) References Cited

U.S. PATENT DOCUMENTS

| | | | |
|---|---|---|---|
| 6,409,722 | B1 | 6/2002 | Hoey et al. |
| 7,776,037 | B2 | 8/2010 | Odom |

(Continued)

FOREIGN PATENT DOCUMENTS

| | | |
|---|---|---|
| EP | 0694291 A1 | 1/1996 |
| EP | 2486860 A2 | 8/2012 |

OTHER PUBLICATIONS

International Search Report and Written Opinion for Application No. PCT/US2014/069492, dated Apr. 30, 2015. (13 pages).

*Primary Examiner* — Jaymi E Della
(74) *Attorney, Agent, or Firm* — Mintz Levin Cohn Ferris Glovsky and Popeo, P.C.

(57) ABSTRACT

Various surgical devices and methods are provided for monitoring and regulating tissue compression and cutting to improve tissue effect. In general, these devices include a handle portion, an elongate shaft, and an effector disposed at a distal end of the shaft and configured to engage tissue. In one embodiment, one or more sensors can be positioned at various locations on the device and can determine a force applied to tissue engaged by the end effector. When the force exceeds a threshold, a notification signal can be issued to a user. In another embodiment, a sensor can determine an amount of current moving between jaws of the end effector and a controller can slow a speed of the cutting element when the sensed current exceeds a threshold amount.

20 Claims, 9 Drawing Sheets

(51) Int. Cl.
   *A61B 18/00* (2006.01)
   *A61B 90/00* (2016.01)
(52) U.S. Cl.
   CPC .......... *A61B 18/1445* (2013.01); *A61B 34/76* (2016.02); *A61B 2017/00022* (2013.01); *A61B 2017/00115* (2013.01); *A61B 2017/00353* (2013.01); *A61B 2018/0063* (2013.01); *A61B 2018/00601* (2013.01); *A61B 2018/00607* (2013.01); *A61B 2018/00619* (2013.01); *A61B 2018/00696* (2013.01); *A61B 2018/00827* (2013.01); *A61B 2018/00898* (2013.01); *A61B 2018/00922* (2013.01); *A61B 2018/1452* (2013.01); *A61B 2018/1455* (2013.01); *A61B 2090/064* (2016.02); *A61B 2090/065* (2016.02); *A61B 2560/0462* (2013.01); *A61B 2562/0261* (2013.01)
(58) Field of Classification Search
   CPC ........ A61B 2018/00773; A61B 17/295; A61B 2018/00666–00678
   See application file for complete search history.

(56) References Cited

U.S. PATENT DOCUMENTS

| | | |
|---|---|---|
| 8,128,625 B2 | 3/2012 | Odom |
| 8,357,158 B2 | 1/2013 | McKenna et al. |
| 8,357,160 B2 | 1/2013 | Odom |
| 9,802,033 B2 | 10/2017 | Hibner et al. |
| 2007/0043352 A1 | 2/2007 | Garrison et al. |
| 2007/0078484 A1 | 4/2007 | Talarico et al. |
| 2008/0039836 A1 | 2/2008 | Odom et al. |
| 2008/0132893 A1 | 6/2008 | D'Amelio et al. |
| 2009/0076534 A1* | 3/2009 | Shelton, IV ...... A61B 17/07207 606/170 |
| 2009/0138006 A1 | 5/2009 | Bales et al. |
| 2010/0217264 A1 | 8/2010 | Odom et al. |
| 2012/0022525 A1 | 1/2012 | Dietz et al. |
| 2012/0022527 A1* | 1/2012 | Woodruff ............ A61B 18/1445 606/45 |
| 2012/0022529 A1 | 1/2012 | Shelton, IV et al. |
| 2012/0078139 A1 | 3/2012 | Aldridge et al. |
| 2012/0101488 A1 | 4/2012 | Aldridge et al. |
| 2012/0116379 A1* | 5/2012 | Yates ..................... A61B 34/25 606/33 |
| 2012/0116391 A1 | 5/2012 | Houser et al. |
| 2012/0143182 A1 | 6/2012 | Ullrich et al. |
| 2012/0172873 A1 | 7/2012 | Artale et al. |
| 2013/0338665 A1* | 12/2013 | Tanaka ............... A61B 18/1206 606/41 |
| 2014/0246473 A1* | 9/2014 | Auld ..................... A61B 90/98 227/175.1 |
| 2015/0005768 A1 | 1/2015 | Sutherland et al. |

\* cited by examiner

SURGICAL DEVICES HAVING CONTROLLED TISSUE CUTTING AND SEALING

CROSS REFERENCE TO RELATED APPLICATIONS

The present application is a continuation of U.S. patent application Ser. No. 14/166,194 entitled "Surgical Devices Having Controlled Tissue Cutting And Sealing" filed Jan. 28, 2014, which is hereby incorporated by reference in its entirety.

FIELD

The present invention relates to surgical devices having mechanisms for cutting and sealing tissue, and methods of using the same.

BACKGROUND

Various surgical devices are used for compressing and cutting different types of tissue. In general, these devices have jaws configured to grasp tissue and a cutting mechanism configured to be advanced through the tissue to sever it. These devices can also apply energy to the tissue disposed between the jaws to promote hemostasis.

A common concern when using any of these devices is achieving hemostasis so that bleeding of the target tissue is limited. By increasing the amount of pressure applied to the target tissue, the flow of blood can be limited, decreasing the time necessary to achieve hemostasis. However, applying too much pressure can result in an unnecessary reduction in blood flow to the tissue surrounding the cut-line, potentially resulting in an elevated level of necrosis, a slower rate of healing, and/or a greater recovery period. An optimal amount of force depends on various factors, including the type of tissue and its thickness.

Accordingly, there remains a need for improved surgical devices having controlled tissue compression and cutting, and methods of using the same.

SUMMARY

Various surgical devices are provided herein. In one embodiment, a surgical device is provided that includes a proximal handle portion, an elongate shaft, and an end effector. The proximal handle portion can includes a motor and the elongate shaft can extend distally from the handle portion. The end effector can include first and second jaws disposed at a distal end of the elongate shaft and configured to engage tissue therebetween. The device can further include an actuator configured to receive an input of pressure from a user that causes the motor to provide power to cause at least one of the first and second jaws to move such that a distance between the first and second jaws is reduced and to advance the cutting element. At least one sensor can be disposed on at least one of the jaws, the sensor being configured to determine a force applied to tissue disposed between the jaws when the jaws are caused to compress tissue disposed therebetween. A controller can be configured to determine when the force exceeds a predetermined threshold and, if the force is in excess of the predetermined threshold, to cause a notification signal to be issued to a user.

The device can vary in any number of ways. The handle portion can include a power source that is electrically coupled to the at least one sensor. In certain aspects, the at least one sensor can include at least one strain gauge. In other aspects, the at least one sensor can include first and second strain gauges. The at least one strain gauge can be positioned parallel to a longitudinal axis of the first and second jaws. The first strain gauge can be positioned on the first jaw and the second strain gauge is positioned on the second jaw. The first and second gauges can be wired in parallel so that if one strain gauge fails, the device is still configured to measure a strain.

The notification signal can vary in any number of ways. For example, the notification signal can include an audible signal. In certain aspects, the notification signal can activate a visual indicator disposed on the handle portion. In other aspects, the notification signal can be configured to provide a tactile sensation to a user. For another example, the notification signal can include a vibration.

The predetermined threshold force can depend on at least one of tissue type and tissue thickness. In one embodiment, when the force applied to the tissue exceeds the predetermined threshold, the actuator can be configured to automatically fix a relative position of the first and second jaws.

In another embodiment, a surgical device can include a proximal handle portion that includes a motor, an elongate shaft extending distally from the handle portion, and an end effector having first and second jaws pivotably coupled to a distal end of the elongate shaft. The first and second jaws can include first and second electrodes configured to apply energy to tissue disposed therebetween. An actuator can be configured to receive an input of pressure from a user that causes the motor to provide power to advance a cutting element. A sensor can be configured to sense current moving between the first and second electrodes, and a controller can be configured to slow a speed of the cutting element when the sensed current exceeds a threshold amount.

The actuator can be configured to control opening and closing of the first and second jaws. A sensor can be configured to determine a relative position of the first and second jaws. The first and second electrodes can be configured to apply RF energy to tissue disposed therebetween.

A surgical method is provided herein that includes engaging a tissue between first and second jaws of an end effector of a surgical device and applying energy to a portion of the tissue positioned between the end effector. The method can include causing a motor of the device to supply power to a cutting element of the device such that the cutting element advances through the tissue so as to cut the tissue. When the cutting element is advancing through the tissue, an amount of the applied energy traveling through the portion of tissue engaged by the end effector can be sensed and a control signal can be generated in response, the control signal modulating an amount of the power supplied to the motor so as to adjust a speed of the cutting element. In certain aspects, the applied energy traveling through the tissue includes electrical current.

In another embodiment, a surgical method is provided that includes engaging a tissue between first and second jaws of an end effector of a surgical device and measuring a force applied to the tissue by the first and second jaws. When the measured force exceeds a predetermined threshold force, the method can include generating a notification signal to alert a user. In certain aspects, the predetermined threshold force is inputted into the surgical device by a user.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various surgical devices are provided for monitoring and regulating tissue compression and cutting to improve tissue effect. The surgical devices herein generally include a handle portion, an elongate shaft, and an effector having first and second jaws configured to engage tissue therebetween. One or more sensors can be positioned at various locations on the device and can be configured to obtain data indicative of tissue type, thickness, etc. For example, in one embodiment at least one sensor can be used to calculate a force applied to tissue engaged by the end effector. In another embodiment, the surgical device can be configured to apply energy to the tissue in the form of electrical current and one or more sensors can measure an amount of current moving between jaws of the end effector. In use, these surgical devices can adjust operational characteristics based on this feedback in order to facilitate hemostasis of the tissue.

Figure 1:
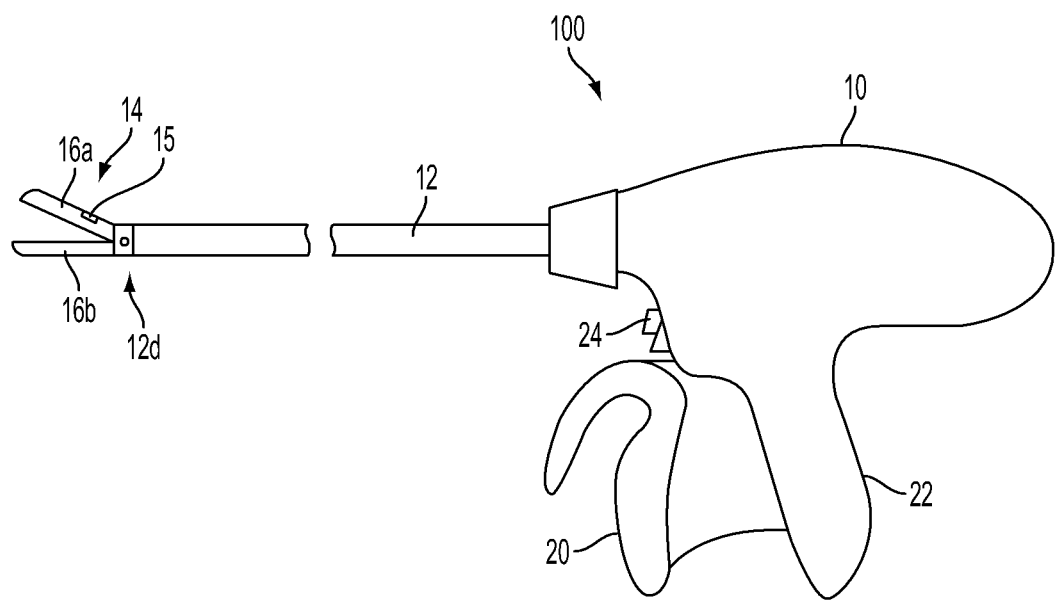
FIG. 1 is a side view of one embodiment of a surgical device.

FIG. 1 illustrates one embodiment of a surgical device configured to grasp and cut tissue. A surgical device 100 can generally include a proximal handle portion 10, a shaft portion 12, and an end effector 14 for grasping tissue. The proximal handle portion 10 can be any type of pistol-grip or other type of handle known in the art that is configured to carry various actuators, such as actuator levers, triggers or sliders for actuating the end effector 14. In the illustrated embodiment, the proximal handle portion 10 includes a closure grip 20 and a stationary grip 22, and movement of the closure grip 20 toward and away from the stationary grip 22 adjusts a position of the end effector 14. The shaft portion 12 extends distally from the proximal handle portion and can have a bore (not shown) extending therethrough for carrying mechanisms for actuating the jaws. As will be explained in greater detail below, one or more sensors can be positioned on the surgical device and can be configured to sense data related to an applied force on tissue manipulated by the end effector 14. In the illustrated embodiment, the device 100 includes a sensor 15 positioned on the end effector 14.

Figure 2:
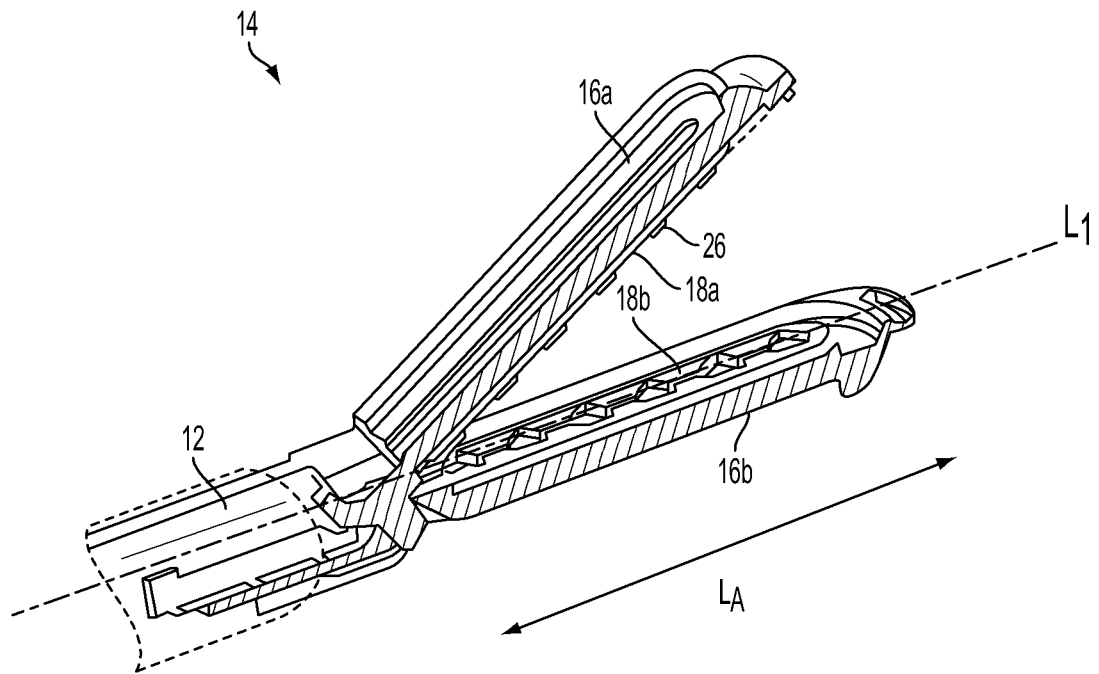
FIG. 2 is a perspective view of the end effector of FIG. 1 in an open position.

The end effector can have a variety of sizes, shapes, and configurations. As shown in FIG. 1, the end effector 14 can include first and second jaws 16a, 16b disposed at a distal end 12d of the shaft portion 12. As can be seen in FIG. 2, the end effector 14 can include a first, upper jaw 16a and second, lower jaw 16b, one or both of which can be configured to close or approximate about an axis. Both of the jaws 16a, 16b can be moveable relative to the shaft portion 12 or alternatively a single jaw can rotate so that the end effector 14 can move between a first, open position in which the jaws 16a, 16b are positioned at a distance apart to a second, closed position in which the jaws 16a, 16b are moved toward one another and are substantially opposed. When the jaws 16a, 16b are in the second, closed position, a longitudinal axis of the upper jaw 16a can be substantially parallel to a longitudinal axis of the lower jaw 16b and the jaws 16a, 16b can be in direct contact. In the illustrated embodiment, the upper jaw 16a can pivot relative to the shaft portion 12 and relative to the lower jaw 16b while the lower jaw 16b remains stationary. In the illustrated embodiment, the jaws 16a, 16b have a substantially elongate and straight shape, but a person skilled in the art will appreciate that one or both of the jaws 16a, 16b can be curved along axis $L_1$. The jaws 16a, 16b can have any suitable axial length $L_A$ for engaging tissue, where the axial length $L_A$ is measured along a longitudinal axis $L_1$ of the end effector 14, as shown in FIG. 2. The axial length $L_A$ of the jaws 16a, 16b can also be selected based on the targeted anatomical structure for transection and/or sealing.

The jaws 16a, 16b can have any combination of features configured to facilitate grasping tissue therebetween. The first jaw 16a can have a first inner engagement surface 18a and the second jaw 16b can have a second inner engagement surface 18b, both of the first and second engagement surfaces 18a, 18b being configured to directly contact tissue. Either one or both of the engagement surfaces 18a, 18b can include one or more surface features formed thereon that can help secure the tissue thereon. For example, the surface features can include various surface features, such as teeth, ridges, or depressions, configured to increase friction between the tissue and the engagement surfaces 18a, 18b of the jaws 16a, 16b without tearing or otherwise damaging the tissue in contact with such surface features. FIG. 2 illustrates a plurality of teeth 26 positioned along an axial length of both of the engagement surfaces 18a, 18b and can facilitate grasping tissue and forming substantially smooth, uniform layers of tissue to improve tissue effect. The first and second jaws 16a, 16b can optionally include features for interacting with a compression member (not shown) configured to apply compressive forces on tissue. For example, the first and second jaws 16a, 16b include first and second recessed slots (not shown) that can receive portions of a compression member and act as a track to direct movement of the compression member. As another example, the first and second recessed slots can be configured to receive portions of a cutting member, as will be discussed in greater detail below.

Figure 3:
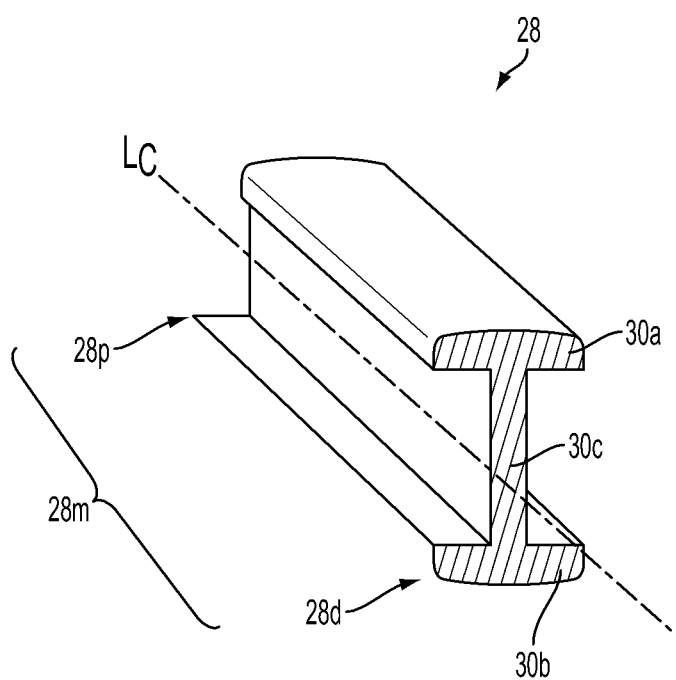
FIG. 3 is a perspective view of an exemplary compression member configured to apply a compressive force on tissue.

A compression member can have various sizes, shapes, and configurations. In general, a compression member can have an elongate shape and can be moveable proximally and distally along the longitudinal axis $L_1$ of the end effector 14. An exemplary compression member 28 is illustrated in FIG. 3. As shown, the compression member 28 can have a proximal end 28p, a medial portion 28m, and a distal end 28d. The proximal end 28p and the medial portion 28m of the compression member 28 can be sized and shaped to reciprocate within the shaft portion 12 of the device 100, while the distal end 28d of the compression member 28 can be sized and shaped to interact with the jaws 16a, 16b of the end effector 14. A longitudinal axis $L_C$ of the compression member 28 can be aligned and coaxial with longitudinal axis $L_1$ of the end effector 14 and of the shaft portion 12, though other configurations are possible. The compression member 28 can be actuatable from the proximal handle portion of the instrument by any suitable mechanism that is operatively coupled to the proximal end 28p of the compression member 28, such as via the firing button 24 shown in FIG. 1. The compression member 28 can include a connecting portion 30c and upper and lower flanges 30a, 30b thus providing an "I-beam" type cross-sectional shape at the distal end 28d of the compression member 28. In the illustrated embodiment, the upper and lower flanges 30a, 30b are positioned substantially perpendicular to the connecting portion 30c to form the "I-beam" shape. As previously mentioned, the upper and lower flanges 30a,30b are sized an shaped to slide in the recessed slots in each of the upper and lower jaw 16a, 16b, and this sliding contact of lateral edges of the flanges 30a, 30b and sides of each of the recessed slot portions prevents lateral flexing of the jaws 16a, 16b. The compression member 28 can have various other configurations. For example, the upper flange 30a can have a width that is greater than a width of the lower flange 30b, the widths being measured in a direction perpendicular to the longitudinal axis $L_1$ of the end effector 14. The compression member 28 can vary in any number of ways and need not be limited to the illustrated embodiment. For example, the upper and lower flanges 30a, 30b can be disposed on the distal end 28d of the compression member 28 and need not extend from the proximal end 28p to the distal end 28d of the compression member 28.

The device can include a cutting member configured to transect tissue captured between the jaws, and the cutting member can vary in any number of ways. The cutting member can be sized and shaped to transect or cut various thicknesses and types of tissue positioned between the jaws of the end effector. In an exemplary embodiment, the cutting member is positioned at the distal end 28d of the compression member 28, formed on the connecting portion 30c of the compression member 28. The cutting member can have a sharp or serrated edge configured to transect the tissue. In an exemplary embodiment, the cutting member can be recessed relative to distal ends of upper and lower flanges 30a, 30b of the I-beam compression member 28 so that compression occurs prior to transecting or cutting of the tissue. As will be appreciated by a person skilled in the art, in another embodiment the cutting member can be a knife blade that is not attached to a compression member such that the cutting member can advance and retract relative to the jaws without applying compression to the tissue.

Referring back to FIG. 1, the surgical device 100 can have a closure actuator 22 that can be configured to open and close the jaws 16a, 16b of the end effector 14. Manipulation of the closure actuator can pivot or otherwise move the jaws relative to one another such that the jaws can engage tissue, move anatomical structures, or perform other surgical functions. The closure actuator can have various sizes, shapes, and configurations, but in the illustrated embodiment the closure actuator includes the closure grip 20 and the stationary grip 22. The closure grip 20 can be moveable toward and away from stationary grip 22, such as via pivoting. In particular, the closure grip 20 can have a first position in which it is angularly offset from the stationary grip 22 and the jaws 16a, 16b of the end effector 14 are open. The closure grip 20 can have a second position where it is positioned adjacent to or substantially in contact with the stationary grip 22 and the jaws 16a, 16b of the end effector 14 can engage tissue and apply a force to tissue disposed therebetween. The closure grip 20 can be biased to the first open position with the jaws 16a, 16b of the end effector 14 being open, as shown in FIG. 1. The closure grip 20 can move the jaws 16a, 16b between the open and closed positions using manual or powered components. For example, in manually actuated embodiments, the pivotable arm 20 can be coupled to a gear that interacts with rack extending in the handle and manual movement of the pivotable arm 20 toward the stationary grip 22 can move the rack distally toward the end effector 14, causing a force to be exerted onto the jaws 16a, 16b to close the jaws 16a, 16b. In powered embodiments, a motor can be disposed in the proximal handle portion 10 and manual movement of the pivotable arm 20 can causes a control signal to be sent to the motor, which causes the jaws 16a, 16b to close. The closure grip 20 can interact with one or more locking features (not shown) configured to lock the closure grip 20 relative to the stationary handle 22. For example, the locking feature can automatically engage when the closure grip 20 substantially contacts the stationary handle 22 or the locking feature can automatically engage at each position the closure grip 20 is pivoted through, such as via ratcheting.

As previously mentioned, in certain aspects the surgical device can have a second actuator that can be separate from the closure actuator. Actuator 24 can be configured to advance a cutting member, apply energy to tissue, or both, and is referred to herein as a "firing actuator." The firing actuator 24 can have various sizes, shapes, and configurations but in illustrated embodiment, can include a button or switch that can be depressed by a user. In another embodiment, the firing actuator 24 can include a trigger, switch, etc. that can be pivoted or otherwise moved by a user. Depressing or pivoting the actuator can activate various elements in the device, and can cause the cutting member to advance toward the end effector and/or cause energy to be delivered to the jaws. For example, depressing or pivoting the firing actuator can cause the compression member and/or the cutting member to advance distally and/or retract proximally relative to the jaws 16a, 16b. More specifically, the firing actuator can be in electrical communication with a motor (not shown) disposed in the proximal handle portion 10. The motor can be operatively coupled to the compression member 28 using known components, such as a gear and rack. In this embodiment, activation of the motor can thus advance and/or retract the compression member 28.

As previously mentioned, the surgical device 100 can measure strain at one or more locations thereon and can determine a force applied to tissue based on the measured strain. In general, a higher applied force results in increased tissue compression. Before the tissue is compressed, it has a first thickness and during compression, the jaws 16a, 16b of the device 100 apply a compressive force to the tissue so that the tissue has a second thickness that is smaller than the first thickness. Compression also produces a generally uniform thickness across an axial length of the tissue. Maintaining a proper amount of force and compression on the tissue is an important factor in achieving effective hemostasis and depends in part on tissue type, thickness, and other characteristics that cannot typically be directly measured during a surgical procedure.

Figure 4:
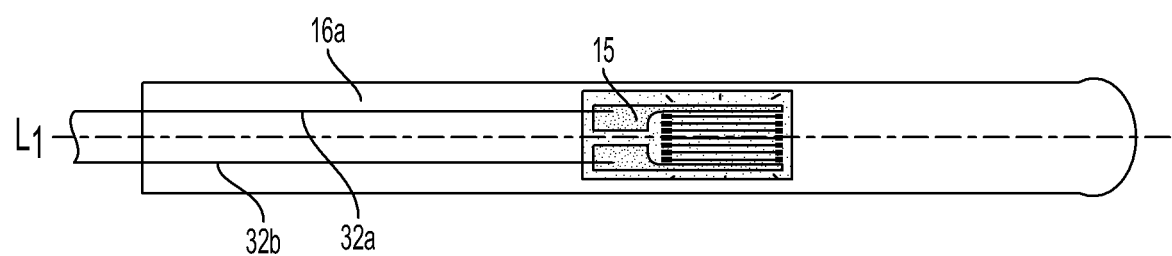
FIG. 4 is a top view of the end effector of FIG. 1 showing a sensor coupled thereto.

The surgical device can include a sensor that can measure strain at one or more locations. In one exemplary embodiment, the sensor can be a strain gauge which measures strain based on deformation of a portion of the device to which it is coupled. The strain gauge can be positioned at various locations on the device, such as on the end effector, on the compression member, on the cutting member, etc. In the embodiment of FIG. 1, a single strain gauge is positioned on an outer surface of the first, upper jaw 16a. Various types of strain gauges can be used to measure strain, as will be appreciated by a person skilled in the art. Exemplary types of strain gauges include a foil strain gauge, semiconductor, piezoelectric, variable capacitance, and/or fiber optic. The strain gauges can be attached to the device using various known techniques, such as using glue, welding, vapor deposition, and/or conductive ink transfer/printing. The strain gauges can be positioned in various orientations on the device, but in a preferred embodiment a longitudinal axis of each gauge is aligned with a direction of strain. For example, as shown in FIG. 4, a longitudinal axis of a strain gauge 15 can be aligned with the longitudinal axis $L_1$ of the end effector 14. The strain gauge(s) can be coupled to a power source in various ways. As shown in FIG. 4, the strain gauge 15 can be connected to first and second leads 32a, 32b. In an exemplary embodiment, power source (not shown), such as a battery, is disposed in the proximal handle portion 10 and leads 32a, 32b extend between the strain gauge 15 and the power source. The leads 32a, 32b can extend through the shaft portion 12, such as in a channel formed in the shaft portion 12 of the device 100 so that the leads 32a, 32b are protected from damage when the shaft portion 12 is positioned in a patient. In another embodiment in which the device is configured to apply energy to tissue, the strain gauge 15 can be electrically coupled to the same power source that generates this energy, such as an RF generator. As will be appreciated by a person skilled in the art, the strain gauge 15 can be coupled to the power source through a separate electrical connection from the RF lines because the strain gauge 15 will require a smaller amount of electrical current than the RF lines.

The surgical device can include any number of strain gauges to assist with measuring an applied force on tissue. For example, a first strain gauge can be positioned on the upper jaw 16a and second strain gauge can be positioned on the lower jaw 16b. Multiple strain gauges can be wired to separate power sources, for example two strain gauges can be wired to two separate power sources, or preferably wired in parallel to the same power source. The use of multiple strain gauges can provide more accurate indication of forces applied to the tissue and can be used to confirm that tissue is engaged and that both jaws 16a, 16b are under strain rather than just a single jaw.

Figure 5:
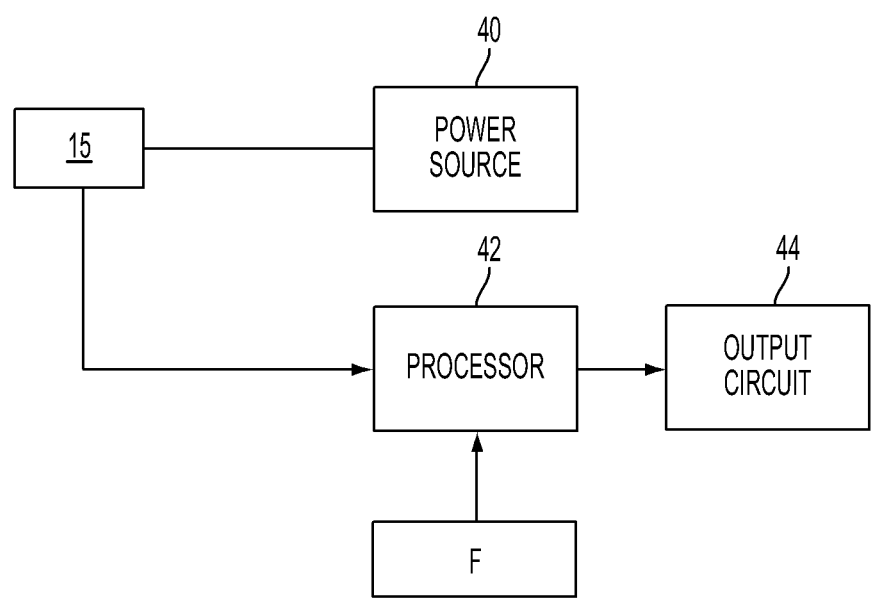
FIG. 5 is a schematic diagram of exemplary components of a surgical device that can receive data and/or adjust based on the compressive force on the tissue.

Additional components can be incorporated into the device to determine a force applied to the tissue by the jaws based on the measured strain and/or to alert a user when the applied force exceeds a predetermined threshold. Exemplary components are shown in FIG. 5, which illustrates the connections between the strain gauge 15 and a power source 40, processor 42, and an output circuit 44. A predetermined threshold force F can be adjusted by a user or can be preset by the device manufacturer. In general, the predetermined threshold force F can vary depending on the intended use of the device 100, e.g. the type of tissue to be cut and/or sealed during a surgical procedure (muscle, bowel, solid organ, etc.) and/or the thickness of the tissue. The predetermined threshold force F can be programmed into the processor 42 of the device 100, as indicated in FIG. 5. In an exemplary embodiment, the processor 42 can be disposed in the proximal handle portion 10, but a person skilled in the art will appreciate that the processor 42 can be positioned at other locations in the device 100 or can be a separate apparatus from the device 100. The strain gauge 15 can communicate with the processor 42 using known techniques, such as via electrical leads, wireless communication, etc. The processor 42 can be configured to analyze the sensed strain data in various ways. In one embodiment, the processor 42 can determine a force applied to tissue based on the sensed strain, and can compare the force to the predetermined threshold force F.

The surgical device can generate one or more signals indicating that a predetermined threshold force is applied to the tissue. The signals can vary in any number of ways, and can be tactile, visual, or audible, and can be generated using known components and techniques, including electrical circuitry. A manual signal can include a vibration. For example, the device can include an indicator that flashes or is otherwise illuminated, and the indicator can be positioned on the proximal handle portion or on any other portion of device that can be visible to a user when the device is positioned within a patient. For another example, an audible signal can include a tone that can be audibly sensed by a user. A person skilled in the art will appreciate that the device can be configured to generate any combination of signals, such as tactile and visual, visual and audible, etc.

A person skilled in the art will appreciate that the particular components used and the connections between the components can vary. In another embodiment (not shown), the surgical device need not directly calculate a force applied to the tissue and thus, need not include the processor. Rather, the strain gauge 15 can be directly wired to the output circuit 44. If the change in resistance of the strain gauge 15 exceeds a threshold amount, this can cause the output circuit 44 to generate the signal to a user. In another embodiment (not shown), the device can include one or more sensors for measuring a distance between the jaws, which can assist in determining an amount of force and/or compression applied to the tissue. By way of non-limiting example, a sensor can measure a distance between the jaws as the jaws move from the open position in which they are spaced apart to a closed position in which they are moved toward one another and engage tissue therebetween. Measurement of such distances can be accomplished using various sensors known in the art, such as a Hall Effect sensor or an optical sensor.

Figure 6:
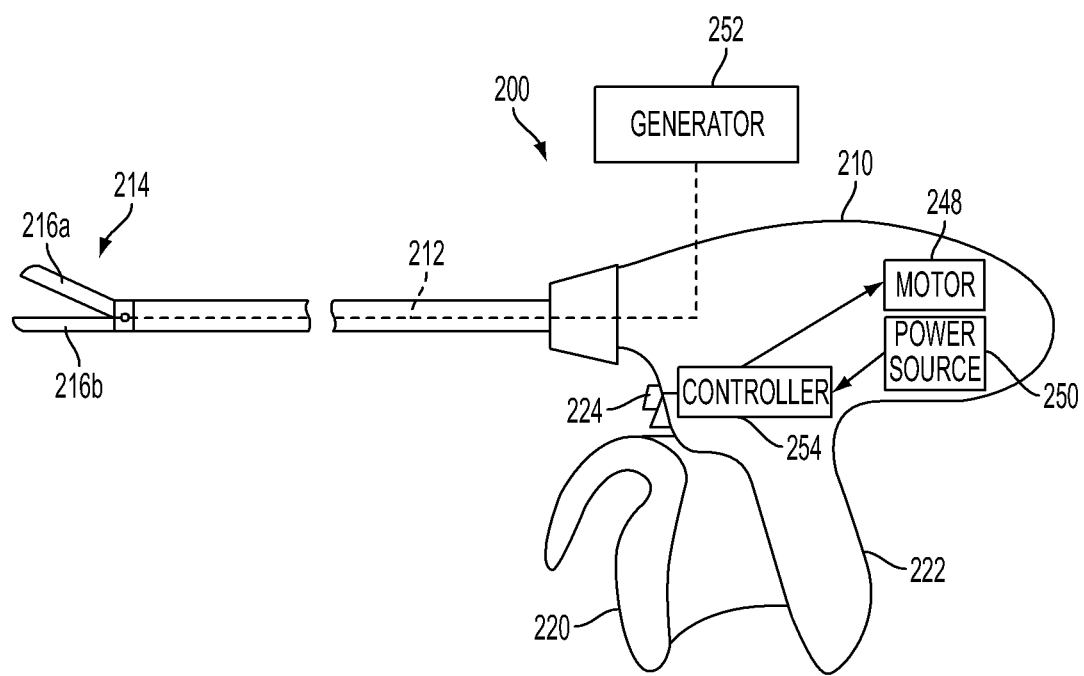
FIG. 6 is a side view of another embodiment of a surgical device.

Another embodiment of a surgical device is shown in FIG. 6. In this embodiment, the surgical device 200 can be configured to apply energy to tissue disposed between first and second jaws 216a, 216b. As previously mentioned, the surgical device 200 can control movement of the cutting member based on tissue thickness in order to improve tissue effect. The surgical device 200 can include many of the features of the device 100 of FIG. 1, including first and second jaws 216a, 216b, shaft portion 212, and proximal handle portion 210. The surgical device 200 can include a cutting member for cutting tissue (not shown), a motor 248, a power source 250, a generator, 252, a controller 254, and optionally a sensor (not shown). The device 200 can also include various components for generating energy and delivering such energy to tissue and these components can be disposed at various locations in the device 200, such as in the proximal handle portion 210 and/or in the jaws 216a, 216b, as will be explained in greater detail below.

The surgical device 200 can include a generator that can be operatively coupled to the firing actuator 224 so that the device is configured to apply energy to tissue. The generator can be any suitable generator known in the art, such as an RF generator 252 shown in FIG. 6. The generator 252 can be a separate unit that is electrically connected to the surgical device 200 to decrease a weight and size profile of the device 200. A bore (not shown) of the shaft portion 212 can carry electrical leads or wires that can deliver electrical energy to components of the end effector 214. As shown, the RF generator 252 can be coupled to the power source 250, such as a battery disposed in the proximal handle portion 210.

Figure 7:
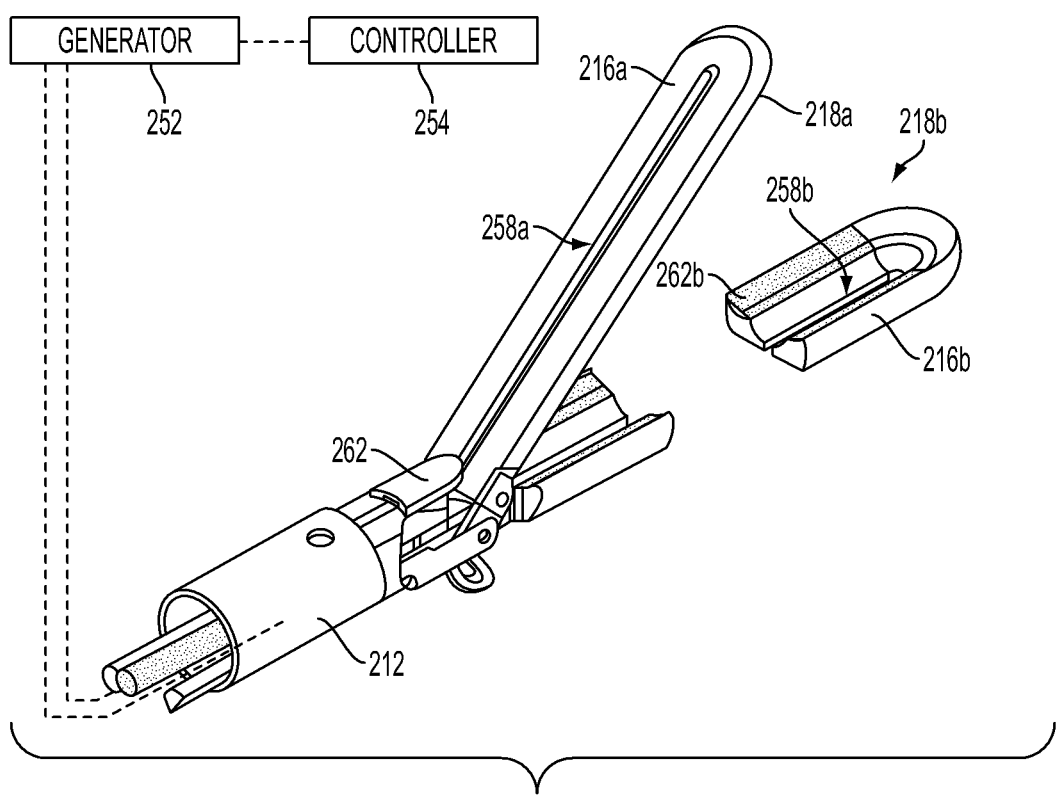
FIG. 7 is perspective view of the end effector of FIG. 6 in an open position.

In general, the end effector 214 of the device 200 can be adapted for transecting captured tissue and for welding the captured tissue margins with controlled application of energy. More specifically, the first and second jaws 216a, 216b can be configured to contact and deliver energy to tissue disposed therebetween. As shown in FIG. 7, the lower jaw 216b can have an engagement surface 218b adapted to deliver energy to tissue and the upper jaw 216a can have an engagement surface 218a adapted to deliver energy to tissue. This energy delivery can be accomplished using various components, such as a variably resistive positive temperature coefficient (PTC) matrix 260a positioned on the upper jaw 216a. An engagement surface 218a of the lower jaw 216b can optionally carry a same or similar type of PTC matrix (not shown). In one embodiment, the engagement surface 218 of the upper jaw 216a includes the PTC matrix 260a while the engagement surface 218b of the lower jaw 216b does not include a matrix. In one embodiment, the PTC matrix 260a is a variably resistive body that comprises a polypropylene or a medical grade silicone polymer that is doped with conductive particles (e.g. carbon). Polymer positive temperature coefficient (PTC) materials, as a person skilled in the art will appreciate, are over current protection devices that will "trip" and become resistant when a selected trip current is exceeded. The lower jaw 216b can further include an electrode 262b, as described in further detail below. The first and second engagement surfaces 218a, 218b can have any of the features of the jaws 16a, 16b, including first and second recessed slots 258a, 258b formed in each of the engagement surfaces 218a, 218b and configured to receive and direct movement of a compression member and/or a cutting member. As shown in FIG. 7, the device 200 can include a compression member 228 that can advance and retract via the recessed slot 258a, or in another embodiment, the device 200 can include a cutting member without a compression member 228, e.g. without upper and lower flanges, such that the device can cut tissue without the cutting member applying a compressive force.

Figure 8:
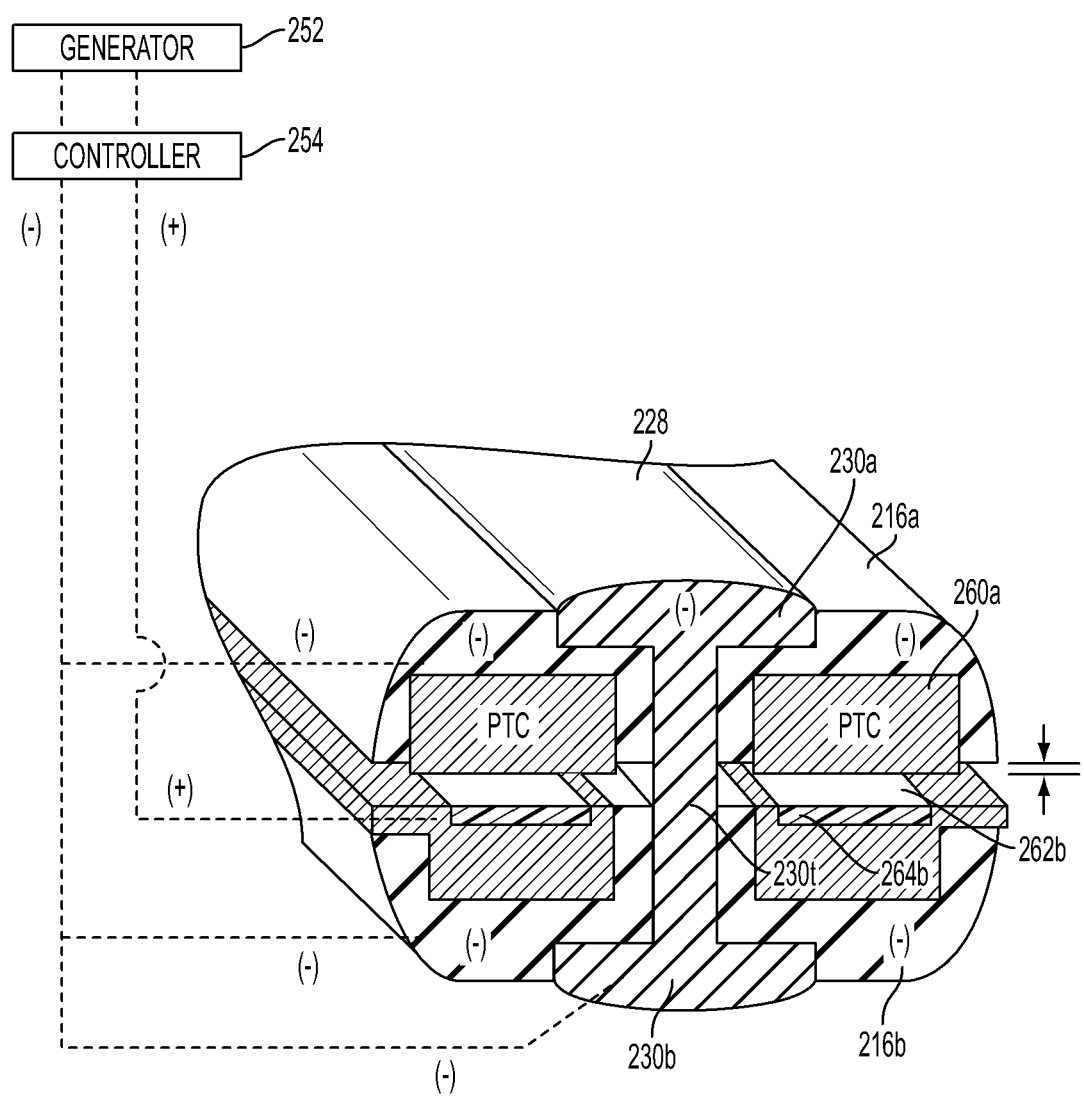
FIG. 8 is a perspective view of the end effector of FIG. 6 in a closed position.

FIG. 8 illustrates the jaws 216a, 216b of device 200 in a closed position. As shown, the engagement surface 218a of the jaw 216a can carry a variable resistive bodies or matrices, such as the PTC matrix 260a described above. The engagement surfaces 218a, 218b can have opposing polarity conductors, also referred to herein as electrode elements, which are coupled to the RF generator 252 and to the controller 254. As shown, the lower jaw 216b can have an electrode element 262b with a positive polarity (+). The electrode element can have a variety of sizes, shapes, and configurations, but in the illustrated embodiment it extends in a "U" shape about the distal end of the recessed slot. The lower jaw 216b can have the electrode element 262b embedded in an insulator 264b that can help insulate the lower jaw 216b from the electrode element 262b to allow the device to operate in bipolar mode to heat and seal tissue. FIG. 8 also shows that the RF source 252 is further coupled to the upper jaw 216a indicated as a negative polarity body. It will be appreciated by a person skilled in the art that the polarities of each of the components of the end effector 14 can be changed to facilitate delivery of electrical energy. The positive (+) and negative (−) labels of are used to illustrate the polarity of the electrodes, but a person skilled in the art will appreciate that any of the illustrated polarities (i.e., the (+) and (−) labels) can be reversed, as current flows between the electrodes in alternating directions. The energy delivered to the jaws 216a, 216b can be controlled using a firing trigger, such as firing actuator 224, as will be described in greater detail below.

Figure 9A:
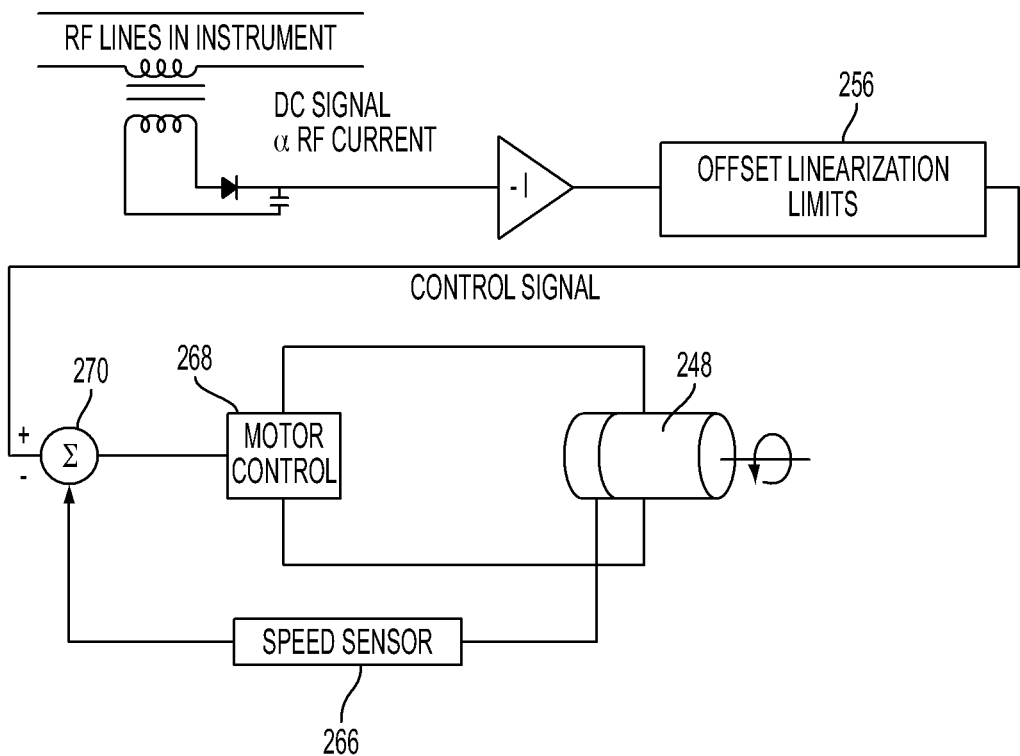
FIG. 9A is a schematic diagram of a control system of the device of FIG. 6.
Figure 9B:
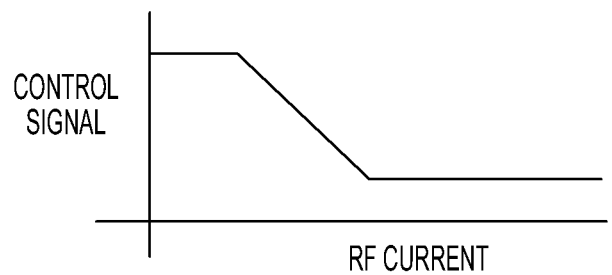
FIG. 9B is a graph showing a relationship between RF current and motor speed.
Figure 9C:
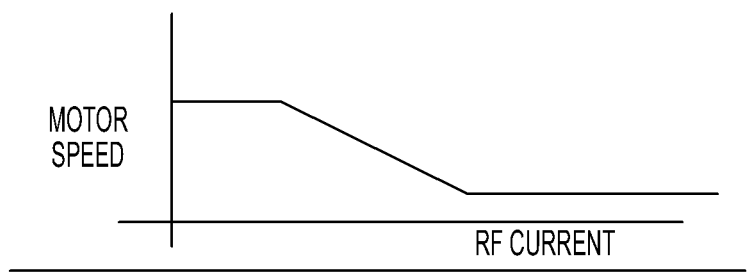
FIG. 9C is a graph showing a relationship between RF current and a control signal.

The surgical device 200 can include a control system configured to measure current traveling between the first and second jaws and configured to control a speed of a cutting element based on the sensed current. For example, one or more sensors 256 can be positioned at various locations on the device and can be configured to measure current traveling between the electrodes of the upper and lower jaws 216a, 216b. The control system can further include a motor speed sensor 266, a motor control 268, the motor 248, and a summa 270. In one embodiment, the sensor(s) can be positioned on either the upper or lower jaw 216a, 216b. Accurately measuring current can facilitate efficient movement of a cutting element and/or compression member through tissue engaged between the jaws 216a, 216b, as an amount of current through the tissue can be directly related to an amount of tissue or tissue load. As shown in FIG. 9A, an amount of current travelling through tissue can be sensed and analyzed using known techniques, such as via the sensor 256, to produce a control signal. In general, the control signal is inversely proportional to an amount of current passing through the tissue, as shown in FIG. 9B, and the speed of the motor 248 is inversely proportional to an amount of current passing through the tissue. In the illustrated embodiment, the control signal can be analyzed by the motor control 268 which determines a speed at which the motor 248 is driven. A high current indicates that there is low impedance or resistance in the tissue and that a high tissue load (e.g. a relatively thick portion of tissue) is engaged between the jaws. In such a case, a speed of the motor 248 should be slowed so that advancement of the cutting member is slowed in order to ensure that the cutting member does not jam when encountering a large thickness of tissue. In an exemplary embodiment, a speed of the motor 248 can be slowed when a calculated impedance of the tissue is less than about 15 ohms. This impedance value is exemplary and persons skilled in the art will appreciate that the speed of the motor 248 can be adjusted based on other values of tissue impedance. Conversely, a low current indicates that there is high impedance or resistance in the tissue and that there is a relatively low tissue load (e.g. a thinner portion of tissue) engaged between the jaws 216a, 216b. In such a case, a speed of the motor 248 should increase to increase a speed of advancement of the cutting member through the tissue engaged by the jaws 216a, 216b. The control signal can directly interact with a motor control 268 that modulates an amount of power provided to the motor 248. As in the illustrated embodiment, the control system can include the comparator 270 that compares an actual rotational speed of the motor 248, as measured by the speed sensor 266, to a desired speed of the motor 248 that is based on the control signal. This can ensure that the cutting member advances through the tissue with an optimal speed to efficiently cut the tissue.

A person skilled in the art will appreciate that the surgical device and the control system can vary in any number of ways. For example, in another embodiment, the control system can include the components of FIG. 9A, but need not include one or more sensors for measuring actual current in the tissue. Instead, the surgical device can directly measure amount of current drawn from the RF generator and can generate a control signal based on this amount.

As will be appreciated by those skilled in the art, the surgical devices 100, 200 provided herein can include any combination of features previously described. In another embodiment, a surgical device (not shown) can include one or more sensors for measuring a force applied by jaws of the end effector and can also be configured to measure a current traveling through tissue engaged by the jaws.

The devices herein can be used to perform a surgical procedure in which tissue is grasped and transected, and optionally sealed using applied energy. A person skilled in the art will appreciate that the procedure is ideally a minimally invasive procedure, but can alternatively be an open surgical procedure. The devices herein can also be used for robotic-assisted minimally invasive or open procedures. The procedure usually begins by preparing the patient for surgery and making one or more appropriately sized incisions at a desired location. In a minimally invasive procedure, one or more cannulas or trocars (not shown) can be positioned in the incisions to provide access to the surgical. One or more viewing devices, e.g., scopes, can be placed in one of the incisions to allow medical personnel to view the surgical site from outside the body.

Once the patient is prepared for surgery, the surgical device 100 can be inserted through the incision and/or through the cannula and the end effector 14 can be positioned adjacent to a desired tissue to be treated. In an exemplary embodiment, the tissue to be treated can include one or more layers of blood vessels. As the surgical device 100 is being inserted into the patient, the closure grip 20 can be disposed adjacent to the stationary grip 22 so that the jaws 16a, 16b are in a closed position and occupy a smaller amount of space than when they are in an open position. When the jaws 16a, 16b are positioned adjacent to the tissue to be treated, the closure grip 20 can be moved away from the stationary grip 22 and the tissue to be treated can be positioned between the jaws 16a. 16b. Movement of the closure grip 20 toward the stationary grip 22 can close the jaws 16a, 16b so that respective engagement surfaces 18a, 18b are in direct contact with the tissue and the tissue is securely grasped between the jaws 16a, 16b. A position of the jaws 16a, 16b can directly correspond to a position of the closure actuator 20 relative to the stationary grip 22. As a user applies an input pressure to the closure grip 20 to move it relative to the stationary grip 22, one or more sensors can measure a strain on various portions of the device 100, such as strain on one or more of the jaws 16a, 16b. Optionally, the device 100 can utilize a sensor, such as a Hall Effect sensor, that measures a distance between the jaws. The processor can calculate a force applied to the tissue grasped between the jaws 16a, 16b. When the calculated force exceeds a predetermined threshold force that has been inputted by a user or by the device manufacturer, a signal can be sent to activate an output circuit. When the output circuit receives the signal, the output circuit can issue an alert to a user and the alert can be tactile, visual, audible, or any combination thereof. When the alert is received by a user, the closure grip 20 can optionally automatically lock in the current position or alternatively a user can engage one or more locking features configured to fix a position of the closure actuator relative to the stationary grip 22. With the position of the jaws 16a, 16b fixed and having tissue grasped therebetween, a user can engage a firing actuator 24 which can advance the cutting member and/or compression member to cut the tissue. In another embodiment, the device 100 can automatically cause a cutting member and/or a compression member to advance toward the jaws 16a, 16b cut the tissue disposed therebetween. A person skilled in the art will appreciate that, optionally, energy can be applied to the tissue prior to or during transection of the tissue between the jaws 16a, 16b. Application of energy to tissue is described in further detail below with respect to the surgical device 200 shown in FIG. 6.

The surgical device 200 can be inserted into the body using the method described above, but can also apply energy, e.g., RF current, to tissue disposed between the jaws 216a, 216b prior to, during, and/or after transection of the tissue. In use, when tissue is engaged between the jaws 216a, 216b, energy delivery to the conductor element 262b embedded in the insulator 264b in the second lower jaw 216b will initially cause current flow through the hydrated, conductive tissue and to the PTC matrix 260a in the opposing first upper jaw 216 since it maintains a very low base resistance. Some current flow also will follow conductive paths to lateral negative polarity portions of the upper jaw 216a and optionally to the negative polarity compression member 228. RF energy delivery to the conductor element 262b will not cause current flow through adjacent PTC matrix 260a since it maintains a "higher" base resistance. Thus, initial RF energy delivery to active conductor element in FIG. 8 will cause maximum ohmic heating in the engaged tissue—until heat from the tissue is conducted back to the PTC matrix 260a in the upper jaw 216a to then cause the PTC material 260a to reach its switching range. Current will then flow from active conductor element across the lower jaw's PTC matrix 260a. Thereafter, the RF energy delivery will be modulated between the series and parallel circuit portions as the temperatures of the PTC matrix 260a is modulated in response to tissue temperature. It should be appreciated that the above-described modulation of ohmic heating in tissue will occur about highly-localized portions of the engagement surfaces 218a, 218b of the jaws 216a, 216b and will facilitate the tissue reaching hemostasis.

As energy is being applied to the tissue, the control system can measure current traveling between the first and second jaws 216a, 216b and can be configured to control a speed of a cutting element based on the sensed current. For example, the one or more sensors 256 previously described can measure current traveling between the electrodes of the first and second jaws 216a, 216b or alternatively, the surgical device 200 can directly measure the amount of current drawn from the RF generator 252 and can generate a control signal based on this determination. An amount of current travelling through tissue can be sensed and analyzed using known techniques to produce a control signal. In general, the control signal is inversely proportional to an amount of current passing through the tissue, as shown in FIG. 9B. The motor control 268 can analyze the control signal and determine a speed at which the motor 248 should be driven based on this determination. A high current indicates that there is low impedance or resistance in the tissue and that a relatively thick portion of tissue is engaged between the jaws 216a, 216b. In such a case, the motor control 268 will decrease a speed of the motor so that advancement of a cutting member is slowed in order to prevent the cutting member from jamming when encountering a larger amount or load of tissue. In an exemplary embodiment, a speed of the motor 248 can be slowed when a calculated impedance of the tissue is less than about 15 ohms. Conversely, a low current indicates that there is high impedance or resistance in the tissue and that there is a relatively thin portion of tissue engaged between the jaws. In such a case, the motor control 268 can increase a speed of the motor to increase a rate of advancement of the cutting member through the tissue engaged by the jaws 216a, 216b. Optionally, the control signal can directly interact with a motor control 268 which modulates an amount of power provided to the motor 248. In the illustrated embodiment, the comparator 270 can compare an actual rotational speed of the motor 248, as measured by the speed sensor 266, to a desired speed of the motor 248 that is based on the control signal and if the values are not equal, the motor control 268 can send a signal to the motor 248 that adjusts a speed of the motor 248. These steps can be repeated until the actual rotational speed of the motor 248 is substantially equal to the desired rotational speed of the motor 248. This can ensure that the cutting member advances through the tissue with an optimal speed to efficiently cut the tissue. After the cutting member is advanced through the tissue and is retracted proximally, the device 200 can continue to apply energy to the cut tissue or the jaws 216a, 216b can automatically release the tissue.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further, variations will be apparent to one skilled in the art in light of this disclosure and are intended to fall within the scope of the appended claims. Also, elements or steps from one embodiment can be readily recombined with one or more elements or steps from other embodiments.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a proximal handle portion;
   an elongate shaft extending distally from the proximal handle portion;
   an end effector having first and second jaws coupled to a distal end of the elongate shaft, the first jaw including a first electrode element, and the second jaw including a second electrode element;
   an actuator configured to be actuated by a user and thereby cause a motor to provide power to move a cutting element at a speed along the end effector to cut tissue engaged between the first and second jaws;
   a sensor configured to sense current moving between the first and second electrode elements during movement of the cutting element; and
   a controller configured to decrease the speed of the cutting element when the sensed current exceeds a threshold amount such that the cutting element continuously moves along the end effector at a slower speed.

2. The surgical device of claim 1, wherein the controller is configured to decrease the speed of the cutting element by causing a speed of the motor to decrease.

3. The surgical device of claim 1, wherein the actuator is configured to control opening and closing of the first and second jaws.

4. The surgical device of claim 1, wherein the first and second electrodes are configured to apply radiofrequency (RF) energy to the tissue disposed therebetween.

5. The surgical device of claim 1, wherein the controller is included in the proximal handle portion.

6. The surgical device of claim 1, wherein the actuator includes one of a depressible button coupled to the proximal handle portion, a movable switch coupled to the proximal handle portion, and a movable trigger coupled to the proximal handle portion.

7. The surgical device of claim 1, wherein the threshold amount is adjustable by a user of the surgical device.

8. The surgical device of claim 1, wherein the threshold amount is not adjustable by a user of the surgical device.

9. A surgical method, comprising:
   engaging tissue with an end effector of a surgical device;
   determining an amount of current passing through the engaged tissue using a sensor of the surgical device;
   producing a control signal based on the determined amount of current passing through the engaged tissue, the control signal being indicative of a motor speed;
   determining an actual speed of a motor driving movement of a cutting element along the end effector engaging the tissue; and
   comparing the motor speed indicated by the control signal with the determined actual speed, and in response to the motor speed indicated by the control signal not being equal to the determined actual speed, changing the actual speed of the motor.

10. The method of claim 9, wherein determining the speed of the motor includes sensing the speed of a motor with a speed sensor operatively coupled to the motor.

11. The method of claim 9, wherein determining the amount of current passing through the engaged tissue comprises measuring the amount of current passing between upper and lower jaws of the end effector using the sensor of the surgical device.

12. The method of claim 9, wherein determining the amount of current passing through the engaged tissue comprises measuring an amount of current being drawn from a generator providing energy that allows the current to pass through the engaged tissue.

13. The method of claim 9, further comprising repeating the determining of the actual speed and the comparing during the movement of the cutting element to allow repeated changing of the actual speed of the motor during the movement of the cutting element.

14. The method of claim 9, wherein, in response to the motor speed indicated by the control signal being equal to the determined actual speed, maintaining the actual speed of the motor.

15. The method of claim 9, wherein a controller disposed in a handle portion of the surgical device performs the determining and the comparing.

16. A surgical method, comprising:
engaging a tissue between first and second jaws of an end effector of a surgical device;
causing current to move between a first electrode of the first jaw and a second electrode of the second jaw;
causing a motor to provide power to move a cutting element at a speed along the end effector to cut the tissue;
sensing the current moving between the first and second electrodes; and
in response to the sensed current exceeding a threshold amount, decreasing a speed of the motor and thereby cause the speed of the cutting element to decrease until the cutting element is continuously moving at a desired decreased speed.

17. The method of claim 16, wherein a sensor coupled to the end effector senses the current moving between the first and second electrodes, and a controller receives a signal from the sensor and causes the decreasing of the speed of the motor.

18. The method of claim 16, wherein sensing the current includes measuring an amount of current being drawn from a generator providing energy that allows the current to move between the first and second electrodes.

19. The method of claim 16, further comprising receiving an input of pressure from a user on an actuator of the surgical device, wherein the motor is caused to provide the power in response to the receipt of the input of pressure on the actuator.

20. The method of claim 16, wherein the motor is disposed in a proximal handle portion of the surgical device, and a controller that causes the decreasing of the speed of the motor is disposed in the proximal handle portion of the surgical device.

* * * * *